(12) United States Patent
Wang et al.

(10) Patent No.: US 8,453,515 B2
(45) Date of Patent: Jun. 4, 2013

(54) APPARATUS AND METHOD FOR FATIGUE TESTING OF A MATERIAL SPECIMEN IN A HIGH-PRESSURE FLUID ENVIRONMENT

(75) Inventors: Jy-An Wang, Oak Ridge, TN (US); Zhili Feng, Knoxville, TN (US); Lawrence M. Anovitz, Oak Ridge, TN (US); Kenneth C. Liu, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 303 days.

(21) Appl. No.: 12/875,169

(22) Filed: Sep. 3, 2010

(65) Prior Publication Data
US 2012/0055258 A1 Mar. 8, 2012

(51) Int. Cl.
G01N 3/00 (2006.01)

(52) U.S. Cl.
USPC ............................................. 73/807

(58) Field of Classification Search
USPC ................................................. 73/807
See application file for complete search history.

(56) References Cited

U.S. PATENT DOCUMENTS

| | | | | |
|---|---|---|---|---|
| 3,194,062 A * | 7/1965 | Krafft et al. | | 73/798 |
| 3,273,383 A * | 9/1966 | Krafft et al. | | 73/798 |
| 3,382,709 A * | 5/1968 | Sorensen | | 73/761 |
| 3,481,190 A * | 12/1969 | Inoue | | 73/796 |
| 3,908,449 A * | 9/1975 | Zuber | | 73/857 |
| 4,845,995 A * | 7/1989 | Kaste et al. | | 73/794 |
| 5,056,370 A | 10/1991 | Maier | | |
| 5,345,826 A | 9/1994 | Strong | | |
| 7,155,982 B2 | 1/2007 | Oesmann et al. | | |
| 7,409,848 B2 * | 8/2008 | Petrinic et al. | | 73/12.08 |
| 7,506,555 B2 | 3/2009 | Brostmeyer et al. | | |
| 7,975,557 B2 * | 7/2011 | Hohjo et al. | | 73/799 |
| 2007/0169563 A1 | 7/2007 | Hohjo et al. | | |

OTHER PUBLICATIONS

Z. Feng, et al., "High-Pressure Hydrogen Permeation, Diffusion and Transport in Pipeline Steels," Materials Innovations in an Emerging Hydrogen Economy Conference, 2008, HT-DELV-08, p. 15.
M.R. Louthan, "Testing for Hydrogen Embrittlement: A Tutorial," Materials Innovations in an Emerging Hydrogen Economy Conference, 2008, H2-STOR-20, p. 16.
Z. Feng and T. Armstrong, "ORNL Fact sheet: Materials Joining Technology for Hydrogen Delivery Infrastructure".
Zhili Feng, et al., V.A Pipelines: V.A.1 Hydrogen Permeability and Integrity of Hydrogen Transfer Pipelines, 2005.
Z. Feng, et al., Hydrogen Permeability and Integrity of Hydrogen Delivery Pipelines, 2005.
Z. Feng, H2 Permeability and Integrity of Steel Welds, 2008.
David McColskey, et al., "NIST Workshop on Materials Test Procedures for Hydrogen Pipelines," 2007.
Zhili Feng, et al., Permeation, Diffusion, Solubility Measurements: Results and Issues, 2007.

* cited by examiner

*Primary Examiner* — Lisa Caputo
*Assistant Examiner* — Octavia D. Hollington
(74) *Attorney, Agent, or Firm* — Colin L. Cini

(57) ABSTRACT

The invention provides fatigue testing of a material specimen while the specimen is disposed in a high pressure fluid environment. A specimen is placed between receivers in an end cap of a vessel and a piston that is moveable within the vessel. Pressurized fluid is provided to compression and tension chambers defined between the piston and the vessel. When the pressure in the compression chamber is greater than the pressure in the tension chamber, the specimen is subjected to a compression force. When the pressure in the tension chamber is greater than the pressure in the compression chamber, the specimen is subjected to a tension force. While the specimen is subjected to either force, it is also surrounded by the pressurized fluid in the tension chamber. In some examples, the specimen is surrounded by hydrogen.

14 Claims, 3 Drawing Sheets

APPARATUS AND METHOD FOR FATIGUE TESTING OF A MATERIAL SPECIMEN IN A HIGH-PRESSURE FLUID ENVIRONMENT

STATEMENT REGARDING FEDERALLY SPONSORED RESEARCH AND DEVELOPMENT

This invention was made with government support under Contract No. DE-AC05-00OR22725 awarded by the U.S. Department of Energy. The government has certain rights in the invention.

THE NAMES OF THE PARTIES TO A JOINT RESEARCH AGREEMENT

None.

BACKGROUND OF THE INVENTION

1. Field of the Invention

The present disclosure relates to fatigue testing of material specimens, and more specifically to apparatuses and methods for in-situ fatigue testing of material specimens under high fluid pressure conditions.

2. Description of the Related Art

Hybrid fuel cell/electric vehicles convert the chemical energy of hydrogen gas into electrical energy to power the vehicle's electric motor. In order to make these vehicles a viable for everyday transportation, decentralized hydrogen filling stations are needed to ensure hydrogen is available where consumer-demand is. In order for economic distribution, hydrogen must be piped from its point of production to its point of demand. An extensive pipeline infrastructure is thus needed to distribute the hydrogen from the generation plants to the filling stations.

The ASM Materials Handbook lists five specific types of hydrogen induced damage to metals and alloys. These types are: hydrogen embrittlement, hydrogen-induced blistering, cracking from precipitation of internal hydrogen, hydrogen attack, and cracking from hydride formation. Except for hydrogen embrittlement, a phase transformation is coupled to each of the listed hydrogen damages. Hydrogen embrittlement is the result of hydrogen atoms diffusing through the surface of certain materials. The hydrogen atoms can accumulate within the material's microstructure causing increased subsurface pressure and eventually cracks to form. Hydrogen embrittlement is a major concern for hydrogen pipeline material designers, since even a small leak in a pipe wall, a welded connection, a flange or a fastener could lead to a dangerous situation.

Fatigue effects in materials due to hydrogen contact may cause defects which can remain undetected until a catastrophic failure occurs without warning. Applying tensile, compressive, low cycle fatigue and high cycle fatigue loads to characterize the strength of materials is known. Novel apparatuses and techniques for testing materials under adverse conditions such as hydrogen gas contact are presently needed.

BRIEF SUMMARY OF THE INVENTION

Provided are several examples of apparatuses and methods for applying loads to material specimens in pressurized fluid environments. The apparatuses use the fluid pressure as the force for applying the loads to the specimens.

According to an example, an apparatus has a vessel-shaped body with an interior surface defining a volume for holding the pressurized fluid. In some examples, the fluid is highly pressurized hydrogen gas, but other fluids may be also used. The interior surface has a specimen receiver configured to accept a first end of a material specimen. A piston assembly is disposed in the vessel; the piston assembly has a specimen receiver configured to accept a second end of the material specimen. An exterior surface of the piston assembly cooperates with the vessel's interior surface to form a seal. The seal partitions the volume into two chambers: a tensile chamber and a compression chamber.

A first branch conduit (e.g., tensile branch) conveys the fluid from a source into the tensile chamber at a first pressure (P1), and a second branch conduit (e.g., compression branch) conveys the fluid from the source into the compression chamber at a second pressure (P2). A pressure controller regulates the fluid pressures in the first and second branch conduits.

The piston assembly is movable in relation to the vessel when acted upon by the pressurized fluid. The receivers for holding a material specimen move away from one another when the fluid pressure (P1) in the tension chamber is greater than the fluid pressure (P2) in the compression chamber, and the receivers move toward one another when the fluid pressure (P2) in the compression chamber is greater than the fluid pressure (P1) in the tension chamber. By alternating the (P1) and (P2) pressures with the controller, alternating tension and compression loads are applied to a loaded specimen.

Other systems, methods, features and advantages will become apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE SEVERAL VIEWS OF THE DRAWINGS

A more complete understanding of the preferred embodiments will be more readily understood by reference to the following detailed description when considered in conjunction with the accompanying drawings where like numerals indicate common elements among the various figures.

DETAILED DESCRIPTION OF THE INVENTION

Figure 1:
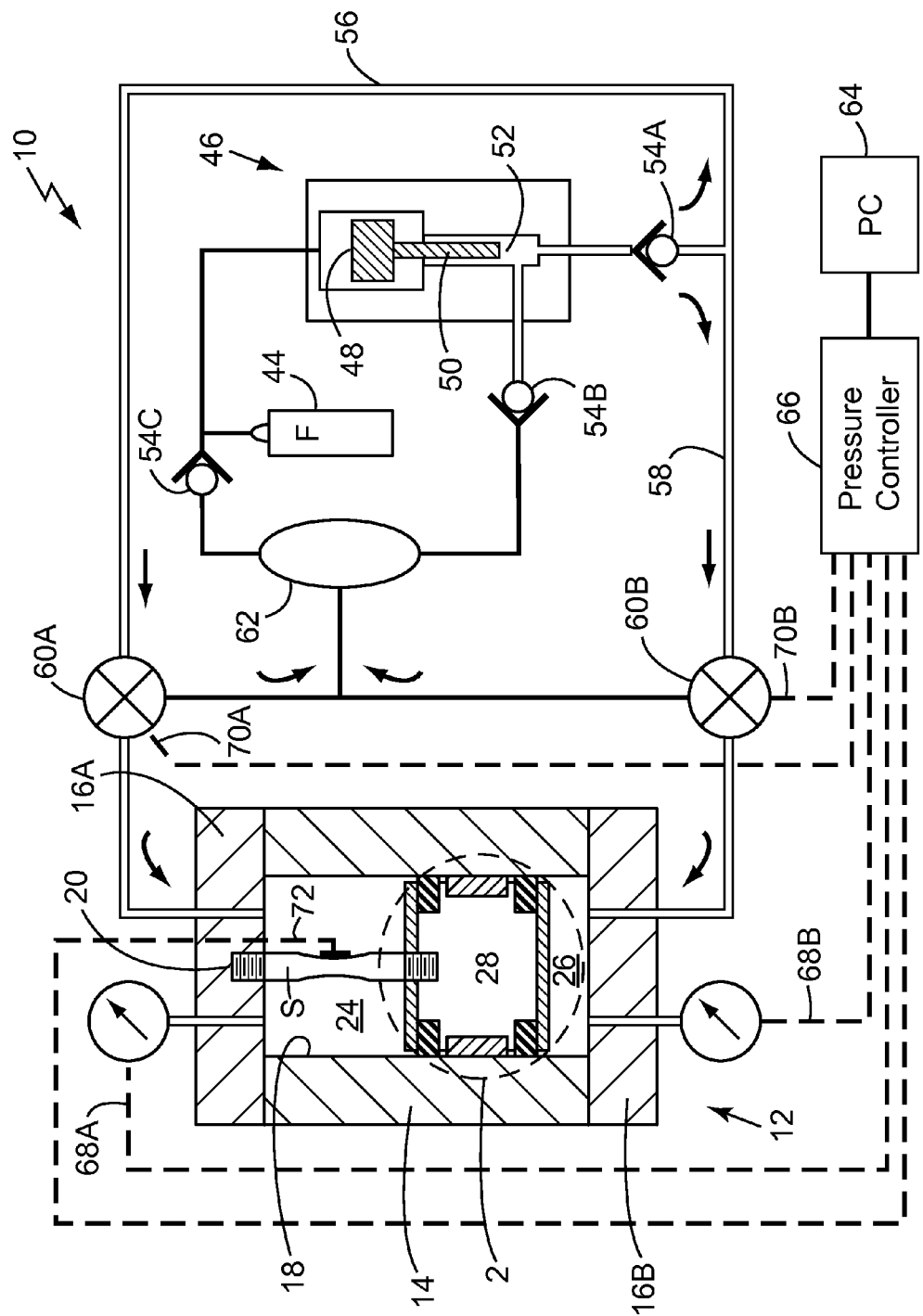
FIG. 1 is a simplified schematic diagram illustrating an example of an apparatus for fatigue testing of material specimens in a high-pressure fluid environment.
Figure 2:
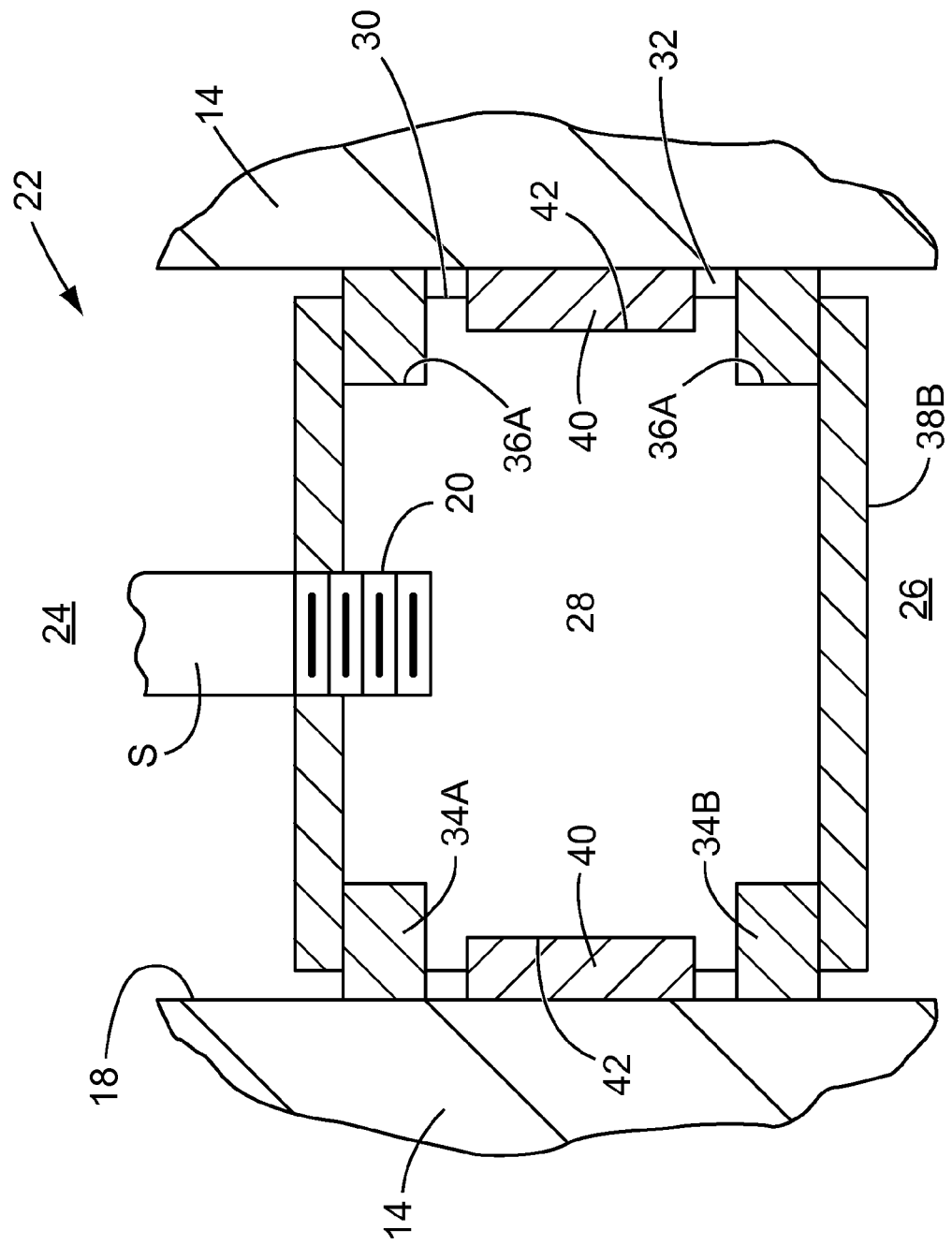
FIG. 2 is a detailed view of the area labeled 2 in FIG. 1.

With reference to FIGS. 1 and 2, an example of an apparatus 10 for fatigue testing of a material specimen S in a high-pressure, fluid F environment is illustrated. As used throughout this disclosure, the term "fluid" encompasses any continuous amorphous substance whose molecules move freely past one another and that assumes the shape of its container; a liquid or a gas. The apparatus 10 utilizes the pressure of the fluid F to impart tensile, compressive and cyclic, fatigue loads in the specimen S. The fluid F imparts the loads while the specimen S is being exposed to the fluid F.

A pressure vessel 12 includes a body 14 and end caps 16A and 16B, which are generally affixed to the body 14 with tie rods, studs, bolts, clamps, threads, welds or other fastening means. In other examples, at least one of the end caps 16A and 16B is integrally formed with the body 14. The vessel 12 has an interior surface 18, defining an enclosed volume, for confining the fluid F such as hydrogen gas for example. In one example, the interior surface 18 is a bore with a cylindrical shape. Although a cylindrical-shaped, thick-walled body 14 and circular-shaped end caps 16A, 16B are commonly used for making pressure vessels, other shapes and configurations are also contemplated in the present examples. The materials, thicknesses and manufacturing methods used to manufacture the body 14 and end caps 16A, 16B are engineered to safely handle the pressure loads imparted by the pressurized fluid F. Pressure vessel design criteria are available through the American Society of Mechanical Engineers (ASME) boiler and pressure vessel code.

A specimen receiver 20 is disposed in at least one of the end caps 16A and 16B, and is configured to accept one end of a mounted specimen S. The receiver 20 may be configured to accept one end of a standard specimen S (e.g., 0.750 inch NC threads), or the receiver 20 may be configured to accept one end of a standard test strip or a specimen S of custom size and shape.

Disposed within the pressure vessel 12 is a piston assembly 22 for partitioning the enclosed volume into two pressure chambers: a tensile chamber 24 and a compression chamber 26. The piston assembly 22 includes a piston body 28 with an external surface 30 that is complementary to the shape of the interior surface 18, and in the example shown; the piston body 28 is cylindrical in shape. A receiver 20 is disposed in the piston body 28 and is configured to accept a second end of a loaded specimen S.

A clearance gap 32, formed between the piston assembly 22 and the interior wall 18, permits the piston assembly 22 to move in relation to the interior wall 18. Sealing elements 34A and 34B are disposed respectively in glands 36A and 36B formed in the external surface 30 of the piston body 28. The sealing elements 34A and 34B span across the clearance gap 32, interacting with the piston body 28 and interior wall 18, to create a fluid F seal. The seal discourages leakage of fluid F between the tensile chamber 24 and the compression chamber 26. The cross section of the sealing elements 34A and 34B may be square, rectangular (shown), circular, oval, or some other shape known in the sealing art. The sealing elements 34A and 34B may be full annular, or segmented annular in form. The material of the sealing elements 34A and 34B is chosen for its fluid compatibility, lubricity, temperature, and pressure capabilities. A material such as polyurethane or carbon provides adequate properties for this particular application.

Fluid F at pressure P1 in the tensile chamber 24 and at pressure P2 in the compression chamber 26 imparts loads on piston faces 38A and 38B of the piston assembly 22. A bearing set 40 centers the piston assembly 22 with the interior surface 18, maintaining a fairly constant clearance gap 32 as the piston assembly 22 moves in relation to the vessel body 14. The bearing set 40 is disposed in a single groove 42 or individual grooves (e.g., pockets) formed in the piston body 28. The bearing set 40 may be full annular, or segmented annular in form. A material such as DuPont TEFLON brand fluoropolymer provides adequate strength and lubricity properties for this particular bearing application.

A fluid F supply source 44 (e.g., tank or bottle) stores the fluid F, for example hydrogen gas, and provides the fluid F to an attached pressure intensifier 46 via a low pressure conduit. The pressure intensifier 46 increases the pressure of the fluid F supply for use in the pressure vessel 12. Within the intensifier 46, fluid F supplied from the supply source 44 acts on a larger piston 48, a force is transferred mechanically through a connecting rod 50 to an adjoined smaller piston 52. The smaller piston 52 area acts on the fluid F, increasing the pressure with the pressure ratio being inversely proportional to the ratio of the two piston areas. The fluid F exits the fluid intensifier 46 via a high pressure conduit to a one-way valve 54A, thus forcing the high pressure fluid F in a direction out of the fluid intensifier 46 and thus preventing back flow.

Downstream of the one-way valve 54A, the fluid F is directed into two separate, high pressure branches: a tension branch 56 and a compression branch 58. The tension branch 56 delivers a first portion of the fluid F to the tension chamber 24 through end cap 16A and the compression branch 58 delivers a second portion of the fluid F to the compression chamber 26 through end cap 16B. The fluid F pressure within the tension chamber 24 and the compression chamber 26 acts on the piston assembly 22 to apply tension and compression loads to a loaded specimen S. In some examples only a tension load is applied. In other examples only a compression load is applied. In yet other examples, alternating tension and compression loads are applied.

Disposed within the tension branch 56 and compression branch 58, are four-way valves 60A and 60B for modulating the fluid F pressures within the tension chamber 24 and compression chamber 26 respectively. Low pressure return branches convey low pressure fluid F from the four-way valves 60A and 60B back to an attached gas collector 62. In turn, the gas collector 62 is attached to the supply source 44 and pressure intensifier 46 through low pressure conduits and one-way valves 54B and 54C.

A control system includes a processor 64 (e.g., a personal computer) attached to an electronic fluid pressure controller 66. The pressure controller 66, in turn, is attached to one or more fluid F pressure transducers 68A, 68B, one or more pressure regulators 70A, 70B, and one or more specimen S strain monitors 72 (e.g., strain gages). In other examples, temperature and/or humidity monitors may also be installed (not shown). A laboratory monitoring and control software program such as LabVIEW, available from National Instruments, may be installed on the processor 64 to allow an operator to easily view a schematic of the apparatus 10, monitor the various pressure transducers 68A, 68B and adjust valve regulators 70A, 70B.

The processor 64 monitors the magnitude of specimen S loading with the strain monitor 72 while simultaneously modulating the four-way valves 60A and 60B with feedback from the pressure regulators 70A, 70B. The processor 64 also monitors the fluid F pressures of the tension chamber 24 and the compression chamber 26 with the pressure transducers 68A and 68B respectively. The specimen S is loaded in tension when the fluid F pressure in the tension chamber 24 exceeds the fluid F pressure in the compression chamber 26; and the specimen S is loaded in compression when the fluid F pressure in the compression chamber 26 exceeds the fluid F pressure in the tension chamber 24.

The apparatus 10 generates in-situ tensile, compressive or cyclic fatigue loading on a specimen S while it's subjected to a high-pressure fluid F environment. The pressure of the fluid F acting on the piston assembly 22 provides the load source for loading the specimen S in tension and compression. No other mechanical means (e.g., lead screws, actuators, etc . . . ) are used for loading the specimen S during testing. The fluid F may be in a liquid or a gas state and in the illustrated example gaseous hydrogen is used.

Figure 3:
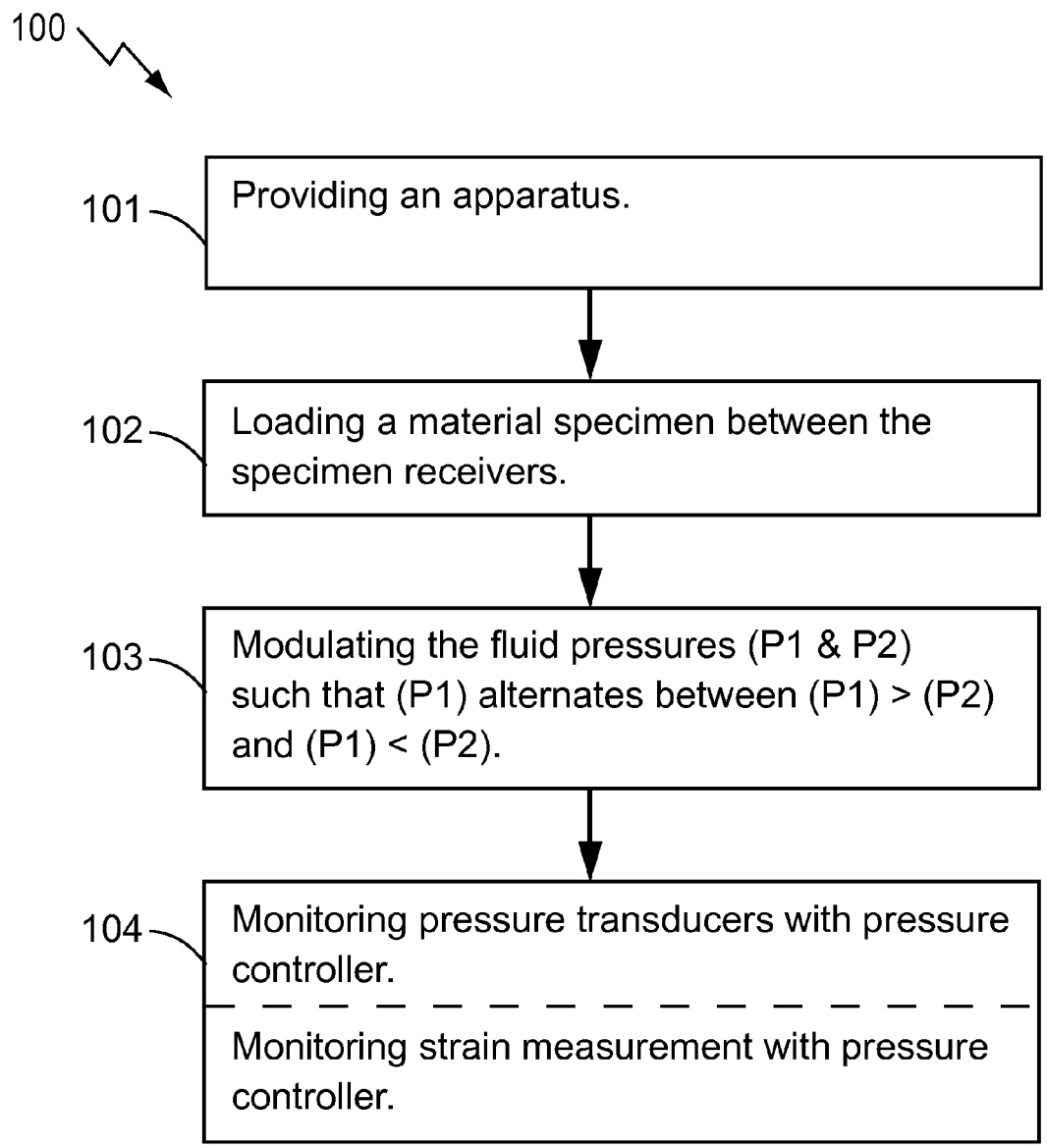
FIG. 3 is a flow diagram illustrating an example of various method steps.

Referring now to the flow diagram of FIG. 3, a method 100 for fatigue testing of a material specimen in a high pressure fluid environment with an apparatus that utilizes the fluid as the load source is now described. In the first process step block labeled 101, an apparatus 10 as previously described above is provided. Next, in the process step block labeled 102, a material specimen S is loaded into the specimen receivers 20. Next, in the process block labeled 103, the fluid pressures in the tension and compression branch conduits 56, 58 are modulated with the pressure controller 66 such that the fluid pressure (P1) in the tension chamber 24 alternates between being greater than and less than the fluid pressure (P2) in the compression chamber 26.

Step 103 may be accomplished by modulating a four-way valve 60A and 60B disposed in each of the tension 56 and the compression branch circuits 58.

The method 100 may also include a step 104 for monitoring pressure transducers 68A and 68B disposed between said pressure controller 66 and each of the tension chamber 24 and the compression chamber 26 with the pressure controller 66. Step 104 may also include monitoring at least one strain measurement from a strain monitor (e.g., strain gage) 72 disposed between the pressure controller 66 and the material specimen S with the pressure controller 66.

While this disclosure illustrates and enables specific examples in the field of material specimen testing, other fields may also benefit. Accordingly, the invention is intended to embrace those alternatives, modifications, equivalents, and variations as fall within the broad scope of the appended claims. The technology disclosed and claimed is available for licensing in specific fields of use by the assignee of record.

The invention claimed is:

1. An apparatus for applying a load to a material specimen while the specimen is exposed to a pressurized fluid environment comprising:
   a vessel having an interior surface defining a volume for holding a pressurized fluid, said interior surface including a specimen receiver configured to accept a first end of a specimen;
   a piston assembly disposed in said vessel, said piston assembly having a specimen receiver configured to accept a second end of a specimen and having an exterior surface that cooperates with the vessel's interior surface to form a seal that partitions the volume into a tensile chamber that exposes the specimen to the pressurized fluid and a compression chamber;
   a tension branch conduit for conveying the fluid from a source into the tensile chamber at a first pressure (P1);
   a compression branch conduit for conveying the fluid from the source into the compression chamber at a second pressure (P2);
   a pressure controller for modulating the pressures of the fluid in the tension and compression branch conduits such that (P1) alternates between (P1)>(P2) and (P1)<(P2); and
   wherein said piston assembly is movable in relation to the vessel when acted upon by the pressurized fluid and the specimen receivers move away from one another when the fluid pressure (P1) in the tension chamber is greater than the fluid pressure (P2) in the compression chamber, and the specimen receivers move toward one another when the fluid pressure (P2) in the compression chamber is greater than the fluid pressure (P1) in the tension chamber.

2. The apparatus as recited in claim 1 wherein said vessel interior surface is cylindrical-shaped.

3. The apparatus as recited in claim 1 wherein said piston assembly includes at least one O-ring disposed between a piston body and the interior surface to prevent leakage of fluid between the chambers.

4. The apparatus as recited in claim 1 wherein said piston assembly includes a bearing disposed between a piston body and the interior surface for aligning said piston assembly with said vessel.

5. The apparatus as recited in claim 1 further comprising pressure transducers disposed between said pressure controller and each of the tension chamber and the compression chamber.

6. The apparatus as recited in claim 1 further comprising a strain monitor for providing strain measurements from a specimen to said pressure controller.

7. The apparatus as recited in claim 1 further comprising a valve disposed in each of said tension branch conduit and said compression branch conduit; and
   wherein said pressure controller regulates the fluid pressure (P1) in the first conduit and the fluid pressure (P2) in the second conduit by modulating said valves.

8. The apparatus as recited in claim 7 wherein said controller modulates said valves such that the fluid pressures (P1) in the tension chamber cycle between being greater than and less than the fluid pressures (P2) in the compression chamber to cycle said piston back and forth within said vessel.

9. The apparatus as recited in claim 1 wherein the fluid F is hydrogen gas.

10. The apparatus as recited in claim 1 further comprising a specimen loaded between the specimen receivers.

11. A method for fatigue testing of a material specimen in a high pressure fluid environment with an apparatus that utilizes the fluid as the load source comprising the steps of:
   a) providing an apparatus as recited in claim 1;
   b) loading a material specimen between the specimen receivers; and
   c) modulating the fluid pressures in the tension and compression branch conduits with said pressure controller such that the fluid pressure (P1) in said tension chamber alternates between being greater than and less than the fluid pressure (P2) in said compression chamber.

12. The method as recited in claim 11, wherein the modulating step further includes modulating a four-way valve disposed in each of the tension and the compression branch circuits.

13. The method as recited in claim 11, further comprising step d) monitoring pressure transducers disposed between said pressure controller and each of said tension chamber and said compression chamber with said pressure controller.

14. The method as recited in claim 13, wherein the monitoring step further comprises monitoring at least one strain measurement from a strain monitor disposed between said pressure controller and the specimen with said pressure controller.

* * * * *

UNITED STATES PATENT AND TRADEMARK OFFICE
CERTIFICATE OF CORRECTION

PATENT NO. : 8,453,515 B2  
APPLICATION NO. : 12/875169  
DATED : June 4, 2013  
INVENTOR(S) : Wang et al.

Page 1 of 1

It is certified that error appears in the above-identified patent and that said Letters Patent is hereby corrected as shown below:

On the Title Page, Item (73) should read

UT-Battelle, LLC, Oak Ridge, TN (US)

Signed and Sealed this  
Sixth Day of August, 2013

Teresa Stanek Rea  
*Acting Director of the United States Patent and Trademark Office*